US010219825B2

United States Patent
Remmerswaal et al.

(10) Patent No.: US 10,219,825 B2
(45) Date of Patent: Mar. 5, 2019

(54) SURGICAL CUTTER (71) Applicant: BasIQ B.V., Delft (NL)

(72) Inventors: Johannes Franciscus Marinus Remmerswaal, Delft (NL); Sebastiaan Veersema, Utrecht (NL); Elinard Wilco Theuvenet, Delft (NL)

(73) Assignee: BasIQ B.V., Delft (NL)

( * ) Notice: Subject to any disclaimer, the term of this patent is extended or adjusted under 35 U.S.C. 154(b) by 571 days.

(21) Appl. No.: 14/653,789

(22) PCT Filed: Dec. 20, 2013

(86) PCT No.: PCT/NL2013/050938
§ 371 (c)(1),
(2) Date: Jun. 18, 2015

(87) PCT Pub. No.: WO2014/098602
PCT Pub. Date: Jun. 26, 2014

(65) Prior Publication Data
US 2015/0342640 A1 Dec. 3, 2015

(30) Foreign Application Priority Data
Dec. 21, 2012 (NL) ..................................... 2010046

(51) Int. Cl.
*A61B 17/3209* (2006.01)
*A61B 17/42* (2006.01)
(Continued)

(52) U.S. Cl.
CPC ...... *A61B 17/3209* (2013.01); *A61B 17/3211* (2013.01); *A61B 17/32093* (2013.01);
(Continued)

(58) Field of Classification Search
CPC .......... A61B 17/3209; A61B 17/32093; A61B 17/322; A61B 17/3211; A61B 17/3201;
(Continued)

(56) References Cited

U.S. PATENT DOCUMENTS 1,918,700 A 7/1933 Harris
2,288,445 A 6/1942 Frizell
(Continued)

FOREIGN PATENT DOCUMENTS

DE 1020070 17 966 B3 11/2008
WO WO-03/011152 A1 2/2003
WO WO-2010/033030 A1 3/2010

OTHER PUBLICATIONS

International Search Report of PCT/NL2013/050938 dated Mar. 21, 2014.

*Primary Examiner* — Darwin Erezo
*Assistant Examiner* — Katherine Schwiker
(74) *Attorney, Agent, or Firm* — N.V. Nederlandsch Octrooibureau; Catherine A. Shultz; Tamara C. Stegmann (57) ABSTRACT A surgical instrument for performing an incision in a portion of a tissue comprises first and second pivoting legs, movable towards each other with respect to a fixed end and defining a receiving space between the legs configured to receive the free edge of the portion of tissue. The surgical instrument has an initial position with relatively opened legs and a closed position, where no further closing movement of the pivoting legs towards each other is possible. A tissue perforating member located at a free end of the first leg extends into the receiving space at a distance from the fixed end, such that when the legs are in the closed position, the tissue can be perforated at a perforation location separated from the free edge of the tissue, while an uncut tissue band remains between the perforation location and the free edge.

5 Claims, 5 Drawing Sheets (51) Int. Cl.
*A61B 17/3211* (2006.01)
*A61B 17/32* (2006.01)

(52) U.S. Cl.
CPC .. *A61B 17/42* (2013.01); *A61B 2017/320052* (2013.01); *A61B 2017/32113* (2013.01)

(58) Field of Classification Search
CPC . A61B 17/122; A61B 17/1227; A61B 17/128; A61B 17/28; A61B 17/2804; A61B 17/2812; A61B 17/2816; A61B 17/282; A61B 17/2833; A61B 17/285; A61B 17/295; A61B 17/30; A61B 17/1285; A61B 2017/32096; A61B 2017/320052; A61B 2017/32113; A61B 2017/00353; A61B 2017/320064; A61B 2017/1225; A61B 2017/2808; A61B 2017/2825; A61B 2017/2829; A61B 2017/2837; A61M 39/284; Y10T 24/44744; Y10T 24/44752; Y10T 24/44761; Y10T 24/44769; Y10T 24/44872; Y10T 24/4488; Y10T 24/44889; Y10T 24/44897; Y10T 24/44906; Y10T 24/44915; Y10T 24/3453; Y10T 24/44265; Y10T 24/44274; Y10T 24/44291; Y10T 24/44316; Y10T 24/44325; Y10T 24/44342; Y10T 24/4435; Y10T 24/44359; Y10T 24/4453; Y10T 24/44538; Y10T 24/44547; Y10T 24/44556
USPC .......................................................... 606/120
See application file for complete search history.

(56) References Cited

U.S. PATENT DOCUMENTS

| | | | |
|---|---|---|---|
| 2,679,249 A | 5/1954 | Weihmann | |
| 3,246,376 A * | 4/1966 | Vazquez | A41F 1/00 24/505 |
| 3,631,858 A | 1/1972 | Ersek | |
| 3,706,312 A * | 12/1972 | Melges | A61B 17/326 606/118 |
| 4,390,019 A * | 6/1983 | LeVeen | A61B 17/122 606/158 |
| 4,579,118 A * | 4/1986 | Failla | A61B 17/122 606/158 |
| 4,938,215 A | 7/1990 | Schulman et al. | |
| 5,046,252 A | 9/1991 | Ayuta et al. | |
| 5,312,420 A | 5/1994 | Toso et al. | |
| 5,667,516 A * | 9/1997 | Allen | A61B 17/122 606/120 |
| 5,922,002 A | 7/1999 | Yoon | |
| 5,984,939 A | 11/1999 | Yoon | |
| 6,348,057 B1 | 2/2002 | Porat | |
| 6,852,117 B2 | 2/2005 | Orlowski | |
| 6,910,401 B2 | 6/2005 | Tapper | |
| 2002/0183771 A1 * | 12/2002 | Burbank | A61B 17/122 606/157 |
| 2003/0004521 A1 * | 1/2003 | Oriowski | A61B 17/122 606/120 |
| 2003/0069589 A1 | 4/2003 | Small | |
| 2003/0074009 A1 * | 4/2003 | Ramsey | A61B 17/122 606/120 |
| 2003/0110898 A1 | 6/2003 | Tapper | |
| 2006/0271074 A1 | 11/2006 | Ewers et al. | |
| 2014/0243862 A1 * | 8/2014 | Bagaoisan | A61B 17/122 606/157 |

* cited by examiner

SURGICAL CUTTER

The present invention relates to a surgical instrument for performing an incision in a portion of a tissue of a human or animal body. In particular, it relates to a type of surgical cutter that can be gripped within a user's hand, comprising first and second pivoting legs movable towards each other with respect to a fixed end and a receiving space between said legs configured to receive a portion of a tissue by a free edge.

BACKGROUND OF INVENTION

A surgical instrument is known from WO2010/033030, where a surgical instrument for performing an episiotomy is disclosed. More specifically, WO2010/033030 discloses an instrument comprising one leg coupled directly to a blade, whereas the other leg is provided with a contra-acting member that acts cooperatively with the perforating member, wherein the position of the blade in respect of the legs is such, that when the blade is moved towards the support surface of the tissue, the tip of the blade near the free end initially comes into contact with the tissue, after which separation or cutting in the direction of the edge of the tissue occurs. This known instrument is designed to be operated by a single hand, e.g. by squeezing the forefinger and middle finger against the thumb. Under certain circumstances, it can be difficult to squeeze the fingers to perform the incision and still keep close control over it or even be able to perform the incision at all. It can be difficult to control the gradual movement of the blade and therefore, control of the cutting action is reduced. If the movement of one leg towards the other is performed too quickly, the desired gradual reduction of tensions at the free edge of the tissue cannot be obtained with the consequence that tension cannot be extenuated in the desired manner This could negatively affect the healing process of the incision. Also, due to this configuration, the medical practitioner could also unintentionally perform the incision following a not desired line.

It would be desirable to provide a surgical instrument that overcomes the previous mentioned drawbacks. Such a surgical instrument should be easily manufactured and can be easily used to perform an incision in a controlled manner.

SUMMARY OF THE INVENTION

According to the present invention, there is provided a surgical instrument for performing an incision in a portion of a tissue comprising first and second pivoting legs movable towards each other with respect to a fixed end, and defining a receiving space between the legs configured to receive the free edge of the portion of tissue, the surgical instrument having an initial position with relatively opened legs and a closed position, where no further closing movement of the pivoting legs towards each other is possible, a tissue perforating member located at a free end of the first leg and extending into the receiving space at a distance from the fixed end, such that when the legs are in the closed position, the tissue can be perforated at a perforation location separated from the free edge of the tissue, while an uncut tissue band remains between the perforation location and the free edge, wherein the perforating member comprises a cutting edge facing the fixed end, such that movement of the surgical instrument in the direction of the free edge will cause incision of the tissue band.

As a result, when closing the legs of the instrument just one perforation at a point located away from the free edge will be made and in order to further perform the incision the medical practitioner needs to move the instrument in the desired direction.

Since two different steps are required, a more controlled incision may be obtained and the risk of an unintentional or too rapid incision is reduced or eliminated. The medical practitioner has also more time after performing the first perforation to revise and control the direction of the incision to be done afterwards.

Preferably, the perforating member is a blade. In this way, performing both steps previously described is facilitated and improved. The blade may be a sharp or scalpel type blade, smooth or serrated and may also be formed of various materials including plastics, metals and ceramics. In particular, the blade may be sharp at both edges, aiding the initial perforation.

An embodiment of the present invention will further include an intermediate third leg in between said first and second legs fixed with respect to the second leg, said receiving space defined by the space between said second and third legs said third leg comprising a slit at its free end for accommodating the perforating member when moving between the initial position and the closed position. Consequently, since the receiving space is defined by two legs which are in relation to each other, it will be easier to accommodate the portion of tissue by its free edge in the surgical instrument.

Advantageously, by providing a surgical instrument whereby said third leg comprises a pivot groove for accommodating a protruding member of the first leg to form a hinge such that the first leg can pivot in relation to the third leg, closing movement of the first leg in respect to the third leg is improved since it is defined by the rotation defined by the described hinge. In embodiments of the invention the surgical instrument defines an initial position whereby said protruding member seats inside said groove forming the hinge and the free end of the first leg engages a safety mechanism at the free end of the third leg to prevent relative pivoting movement of the legs such that the perforating member does not enter the receiving space. Optionally the safety mechanism is an elongated member configured such that when the surgical instrument is in the initial position it covers the perforating member, closing the space between the free ends of the first and third legs. Before starting an incision the medical practitioner will bring the instrument to the initial position knowing that while in this position the perforating member is not in disposition to cut because it is protected by the safety mechanism.

Due to its blocked status, unintentional incisions or accidents can be avoided.

An embodiment of the invention will comprise a surgical instrument wherein the safety mechanism comprises a first detent groove to be engaged by the first leg to keep the instrument in said initial position and advantageously the safety mechanism comprises a second locking groove to be engaged by the first leg to keep the instrument in the closed position. Preferably, the first leg comprises a protrusion at its free end engageable to the safety mechanism. Unintentional movement of the perforating element when in the initial or final configuration can be further avoided such that safety is improved. In particular, the locking groove may reversibly lock the first leg, allowing release e.g. in an emergency. The safety mechanism may comprise a moveable member which may be attached at the free end of the third leg and which is capable of flexing into and out of locking engagement with the first leg. The detent groove and the locking groove can be formed in a surface of the moveable member, which is positioned so that it can be manipulated by the thumb of a user if release from the locking position is required.

To guarantee that initial perforation of the tissue is done only when desired by the medical practitioner an embodiment of the invention describes a surgical instrument wherein the safety mechanism is configured to allow further movement between the intermediate and the closed position when a threshold pressure on the first leg enough to disengage it from the safety mechanism is exceeded. Until sufficient pressure is applied to the first leg, it will not move and the perforating member will remain in its initial position.

Optionally the first leg can comprise an upper biasing member with a protrusion and a lower biasing member with a protrusion to engage the safety mechanism. The upper and lower biasing members with protrusions can engage the safety mechanism such that they can keep the surgical instrument in an initial position and/or in a closed position. The upper and lower biasing members can engage the safety mechanism and bias against each other to ensure that the blade engages the second leg when in the closed position.

Optionally, the surgical instrument can include a safety device that is detachable and can prevent the surgical instrument from going from an initial position to a closed position when the safety device is connected to the surgical instrument. The surgical instrument can connect between the first and third legs and the safety mechanism.

Preferably the claimed surgical instrument is configured to be easily manipulated with a single hand of the medical practitioner such that the first and second legs are provided on the side facing away from the receiving space with elements for accommodating fingers of a hand manipulating the surgical instrument.

In order to further facilitate use and manipulation of the device by a medical practitioner the surgical instrument can comprise the first leg provided on the side facing away from the receiving space with a surface for receiving a thumb of the hand manipulating the instrument and/or the second leg provided on the side facing away from the receiving space with a ridge for defining a finger accommodation on both sides. The instrument will be dimensioned for being held by a user's hand, preferably supported in the arch formed between the thumb and index finger.

In order to obtain a surgical instrument that can be easily manufactured, the surgical instrument of the invention is preferably an injection moulded piece formed unitary with the perforating member. In this context, the blade may be formed of the same material as the rest of the surgical instrument or may be formed of another material, embedded into the first leg during the moulding procedure.

In a further embodiment of the invention the surgical instrument comprises first and second legs pivotably connected to each other at a fixed end for movement between an initial position and a closed position; a tissue perforating member attached to the first leg and extending in a direction of the second leg; an intermediate third leg in between the first and second legs and fixed with respect to the second leg, the third leg comprising a slit for passage of the perforating member, whereby in the initial position, the perforating member occupies a space between the first leg and the third leg and in the closed position the perforating member occupies a space between the third leg and the second leg. Such an arrangement is extremely convenient and ergonomic and is particularly well adapted for the uses as further explained below.

The invention also relates to a method of performing an incision in a portion of a tissue by using a surgical instrument comprising first and second pivoting legs movable towards each other with respect to a fixed end, a receiving space between said legs configured to receive said portion of a tissue by a free edge, said first leg comprising a tissue perforating member within said space, said perforating member comprising a cutting edge facing the fixed end the method comprising introducing the portion of tissue to be cut by its free edge in the receiving space, bringing said legs together to a closed position in order to perforate the portion of tissue only at a point separated from the free edge located in the receiving space and moving the surgical instrument in the direction of the free edge of the tissue to further perform the incision.

Alternatively, methods for performing a caesarean section and for performing an episiotomy are also part of the invention, as included in the appended claims. These methods would improve the control of the instrument by the medical practitioner performing the incision and the gradual reduction of tensions at the free edge of the portion of tissue to be cut.

DETAILED DESCRIPTION

The invention will now be described in more detail below with reference to the exemplary embodiments shown in the drawings, in which.

FIGS. 1 to 5 show a first embodiment of the surgical instrument 1 according to the present invention. It comprises a first pivoting leg 2 comprising at its upper free end a blade 3 substantially perpendicular to said first leg 2 and having a cutting edge 22 directed away from the free end.

Figure 2:
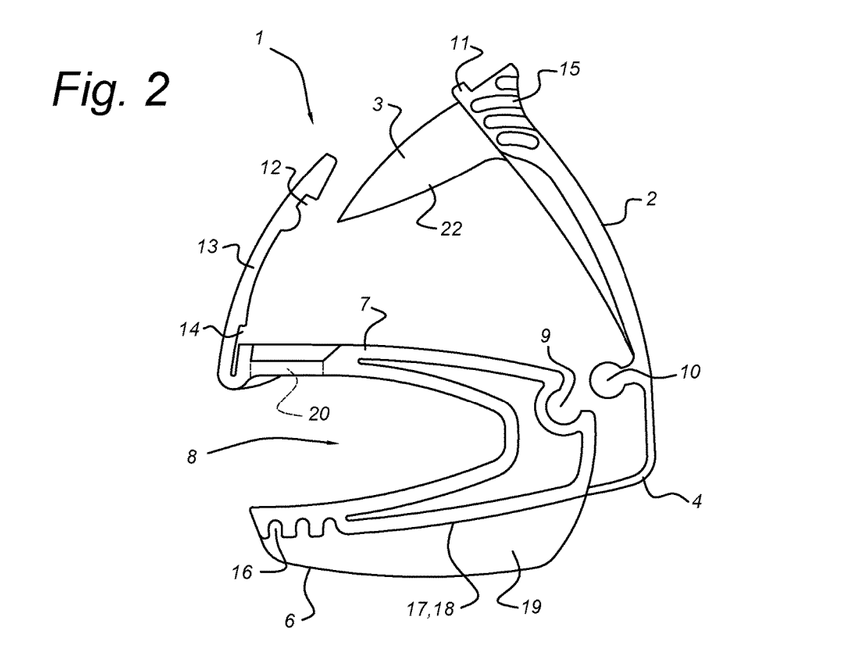
FIG. 2 shows the embodiment of the surgical instrument of FIG. 1 in an as-manufactured position.

FIG. 2 shows an as-manufactured position of the surgical instrument 1 as it might be received from a mould of an injection moulding machine. The first leg 2 is pivotally connected at its lower fixed end 4 to a U-shaped member 5. U-shaped member 5 comprises second leg 6 and third leg 7, the space between second and third legs 6, 7 defining a receiving space 8 for receiving a portion of tissue to be cut by its free edge.

Figure 3:
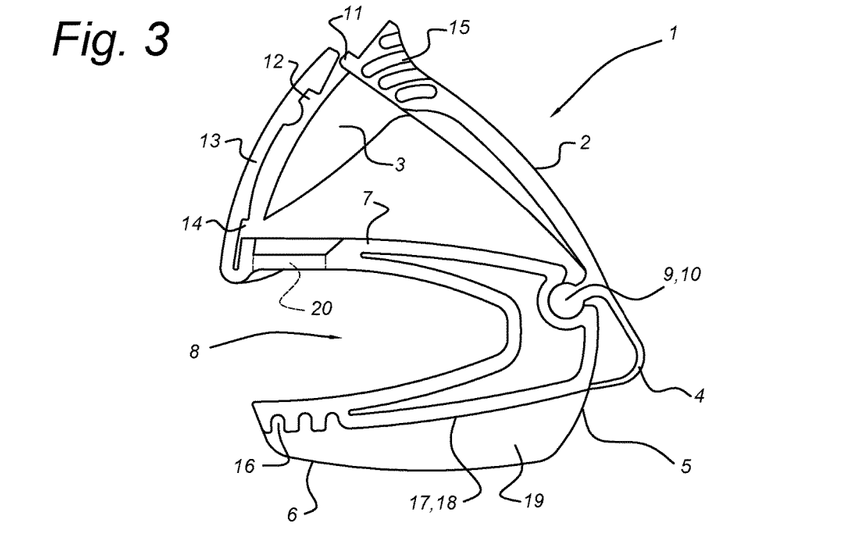
FIG. 3 shows the surgical instrument having a first leg engaged so that it can pivot in respect to the third leg.

As can be seen in the drawings, the U-shaped member 5 comprises on its upper part, corresponding with an end of third leg 7, a concave pivot groove 9. Pivot groove 9 is configured to accommodate protruding cylindrical member 10 on first leg 2. When protruding cylindrical member 10 is received in pivot groove 9 they form a hinge such that first leg 2 can pivot in relation to third leg 7 and U-shaped member 5, as shown in FIG. 3. First leg 2 is flexible in order to allow this pivoting movement.

Third leg 7 of U-shaped member 5 comprises at its free end a safety mechanism for protecting the blade 3 and preventing unintentional cuts of the blade 3. The safety mechanism comprises a flexible elongated member 13 extending upwards, connected at one end to the free end of third leg 7 and describing a curve such that when in the position shown in FIG. 3, the blade 3 will be covered by the elongated member 13.

Figure 4:
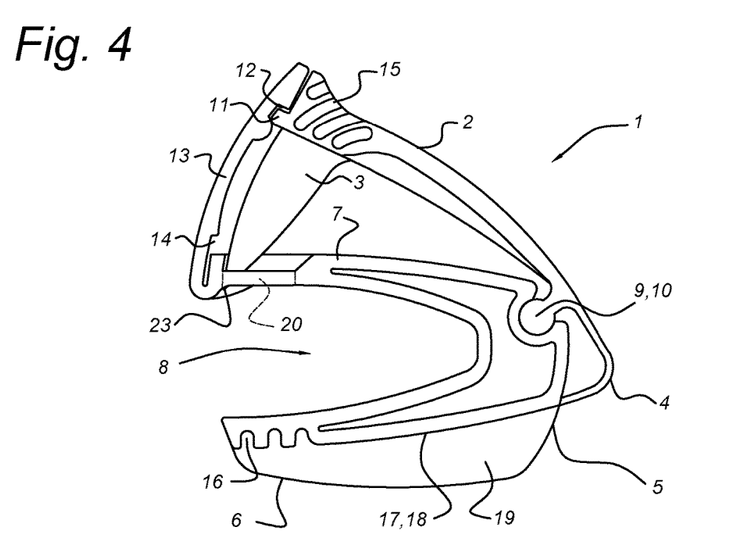
FIG. 4 shows the surgical instrument in the initial position with the blade protected by the safety mechanism.

For using the surgical instrument, first leg 2 will be first brought to an initial position, wherein a protrusion 11 at its free end will engage a first detent groove 12 at the upper end of elongated member 13 of the safety mechanism, as shown in FIG. 4.

Figure 5:
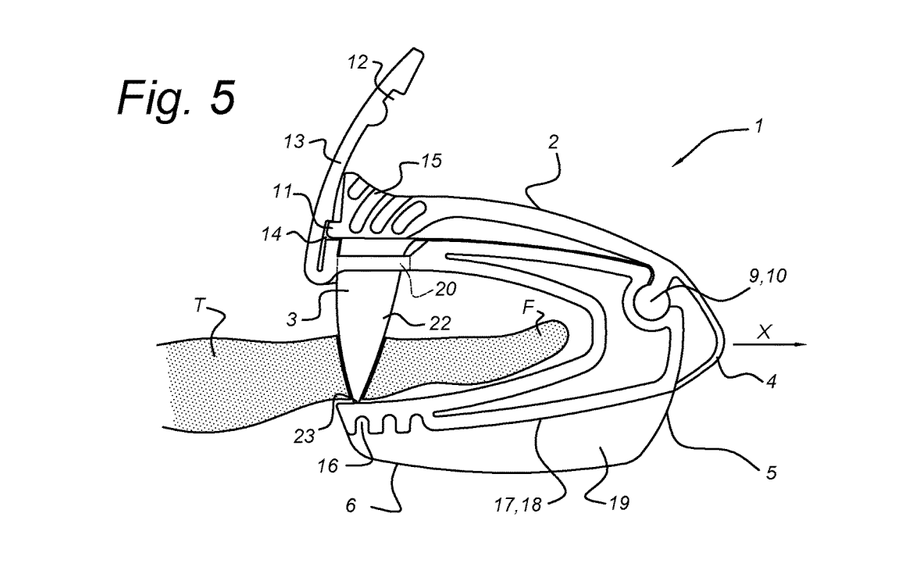
FIG. 5 shows the surgical instrument in the closed position with the blade ready to finalize the incision.

Third leg 7 comprises at its free end, a slit 20 dimensioned to accommodate blade 3, such that blade 3 can pass thorough said slit 20 when first leg 2 is moving from the position shown in FIG. 4 to the closed position shown in FIG. 5.

When first leg 2 is in the initial position shown in FIG. 4, blade 3 does not enter the receiving area between second and first legs 6, 7, and the tip 23 of the blade sits inside slit 20, such that also the tip 23 when the instrument is in the initial position cannot cause any unintentional damage.

First detent groove 12 in the upper part of the elongated member 13 is dimensioned to accommodate protrusion 11 of first leg 2. First detent groove 12 has a first side wall located on the upper part which is perpendicular to its bottom wall in order to retain protrusion 11. Flexed first leg 2, due to its flexing characteristics and pivot around groove 9, as shown in FIG. 4, will be maintained in this initial position due to the counteraction of said first side wall of first detent groove 12. The inclined interior wall of elongated member 13, starting from its upper free end, will facilitate introduction of protrusion 11 into said first detent groove 12 to go from the position of FIG. 3 to the position shown in FIG. 4. Elongated member 13 will also flex to the left to facilitate this. The lower lateral side of first detent groove 12 has a rounded profile such that when first leg 2 is further pressed there will come a moment where protrusion 11 will leave first detent groove 12 by moving downwards around its lower lateral wall making the elongated member 13 flex and move to the left. The threshold pressure necessary to overcome the detent and start movement from the initial position, shown in FIG. 4, to the closed position, shown in FIG. 5, will depend on the flexing characteristics of first leg 2, elongated member 13, and profiles of the detent groove 12 and protrusion 11, which can easily be determined and adapted by the skilled person depending on the needs to avoid any unintentional movement of the blade 3 while in the initial position of FIG. 4.

If the threshold pressure has been exceeded, first leg 2 will move to the closed position shown in FIG. 5. In this position protrusion 11 will enter second locking groove 14 in the lower part of elongated member 13 in order to lock the instrument in this position.

Upper side wall of locking groove 14 is designed to keep protrusion 11 inside it and consequently, first leg 2 in the closed position can only be liberated by deforming the elongated member 13.

Blade 3 is dimensioned such that when in the closed position its tip 23 will engage the upper surface of the second leg 6. Blade tip 23 could also sit inside a slit on the upper surface of second leg 6 in order to guarantee that the blade will perforate the tissue when the tip 23 has reached the bottom of said slit.

According to FIG. 5, the surgical instrument 1 is shown, engaged with a portion of tissue T, having a free edge F. Blade 3 has penetrated the tissue T with its tip 23 and cutting edge 22. In this situation, a band of tissue T lying between the blade 3 and the free edge F of the tissue is still fully intact. In order to further perform the incision, the instrument 1 can be moved in a direction X towards the free edge F. During this movement, the cutting edge 22 of the blade 3 performs the incision. This ensures that the incision is performed from the interior of the portion of the tissue T towards its free edge F.

Figure 1:
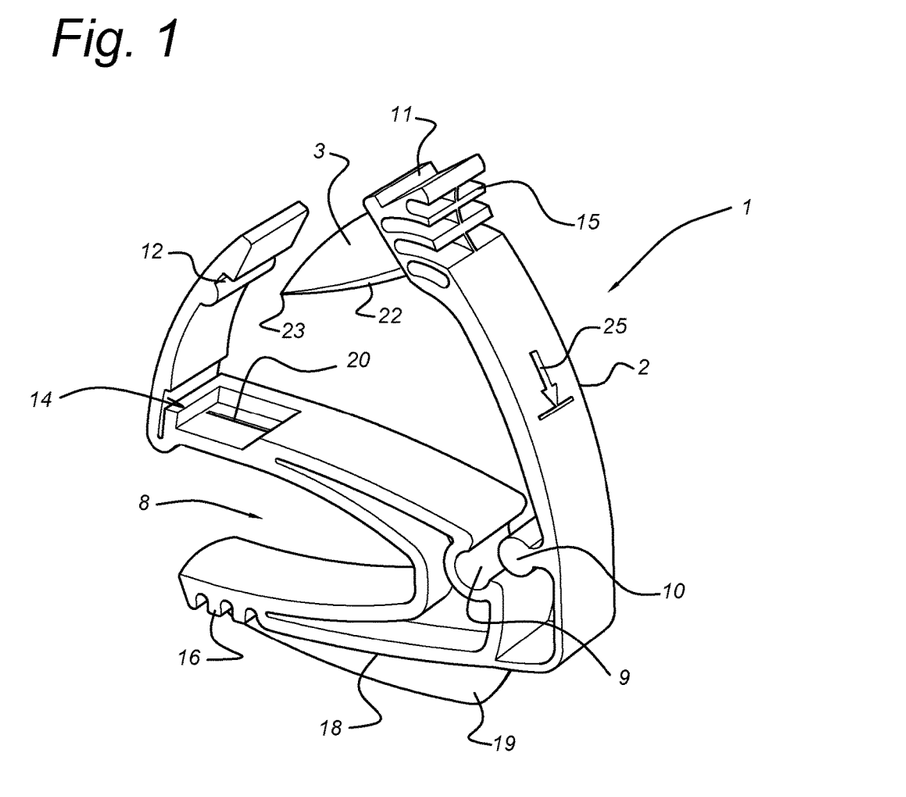
FIG. 1 shows a general overview of an embodiment of the surgical instrument of the present invention.

Surgical instrument 1 is designed to be operated using one hand and therefore, the first leg 1 and second leg 6 are provided on their outer sides facing away from the receiving space with elements for accommodating fingers of a hand manipulating the surgical instrument 1. More specifically, the upper surface 15 of first leg 1 can be adapted to accommodate and receive the thumb of the person using the device and lower surface 16 of second leg 6 can be provided with two lateral supporting surfaces 17 and 18 separated by a ridge 19, which would be engaged by two fingers in touch with supporting surfaces 17 and 18. The presence of the ridge in-between two fingers can also give a better feeling for inserting the second leg 6 in the desired direction. First and second legs 2 and 6, as can be seen in FIG. 1, are preferably provided with a portion of roughened surface 15, 16 at their ends, located in the area where the fingertips of the hand operating the instrument will be located, in order to improve gripping properties and therefore facilitate holding and using the instrument. In this embodiment ridges are provided but other solutions such as different material having improved friction or changing the roughness of the outer surfaces could also be possible.

As described, the surgical instrument is designed to be held with one hand. To facilitate holding and cutting, the upper first leg 2 can be of the same length or longer than the thumb and the lower second leg 6 can be of the same length or shorter than the fingers intended to act on it, generally index and/or middle finger. In this way, when using the instrument to perform an incision by inserting the lower second leg 6 in a cavity of the human body, the medical practitioner can use the fingers on this leg to detect presence of any obstacle, e.g. a part of the foetus when used for performing a caesarean section, that could be damaged by the blade when performing the incision.

To help the medical practitioner estimate the depth of insertion, the upper first leg 2 can be provided with a mark 25 on its upper surface (see FIG. 1). This mark is located at a position corresponding to the end of the receiving space 8. In this way the medical practitioner will know not to continue inserting the instrument when the free edge has touched the inner wall of the receiving space. The mark 25 is in the form of an arrow aligned with the lower second leg 6 and can also help to control the direction of insertion of the device and the direction of cutting.

Advantageously, the instrument 1 is an injection moulded piece which is formed unitary with the blade 3. Alternatively the whole instrument, including the blade, can be an injection moulded piece.

Figure 6:
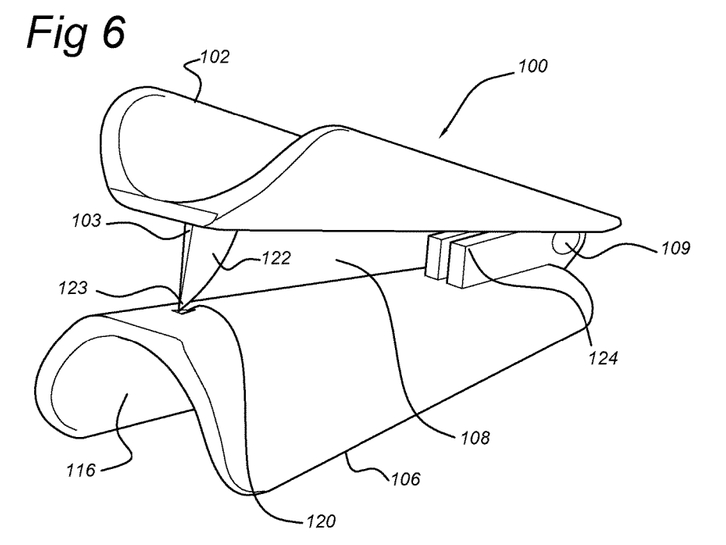
FIG. 6 shows another embodiment of the present invention.

FIG. 6 shows another embodiment of the present invention. The surgical instrument 100 comprises upper 102 and lower 106 pivoting legs with the upper leg 102 having at its upper free end a blade 103 substantially perpendicular to it. The upper and lower legs 102, 106 are joined by a hinge 109. The blade 103 and its cutting edge 122 are distanced from the hinge 109, such that when closing said two pivoting legs 102, 106 a receiving space 108 is defined between the legs 102, 106, the hinge 109 and the blade 103. An abutment 124 is provided adjacent to the hinge 109, which prevents further closure of the legs 102, 106 beyond a point where the blade 103 engages the second lower leg 106. It will be noted that a slot 120 is located in the lower leg 106 to receive a tip 123 of the blade 103. In this embodiment too, the lower leg 106 is provided with a recess 116 for the receipt of a single finger and the lower leg 106 itself is relatively narrow making for easy insertion. As in the previous embodiment, in use for incising a free edge of tissue, the tissue will only be perforated at a point separated from the free edge of the tissue located in the receiving space 108.

Figure 7:
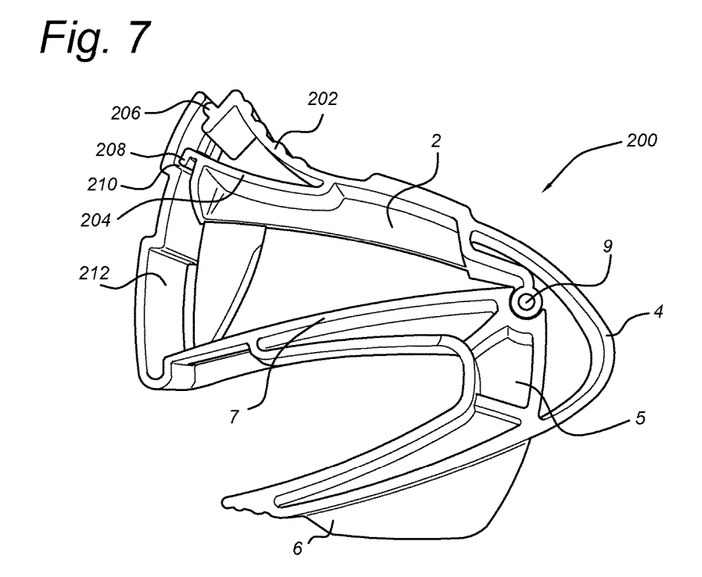
FIG. 7 shows a further embodiment of the present invention in the initial position.
Figure 8:
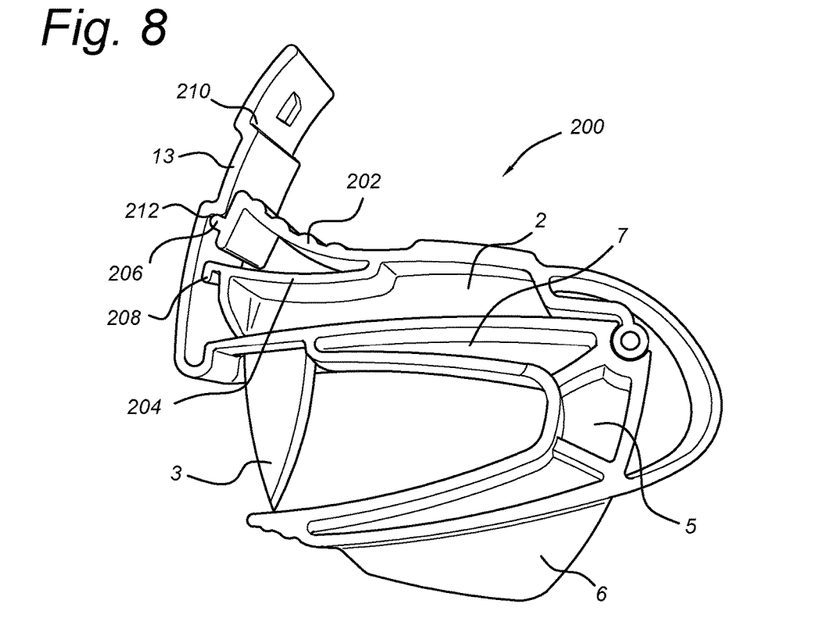
FIG. 8 shows the embodiment of FIG. 7 in the closed position with the blade ready to finalize the incision.
Figure 9:
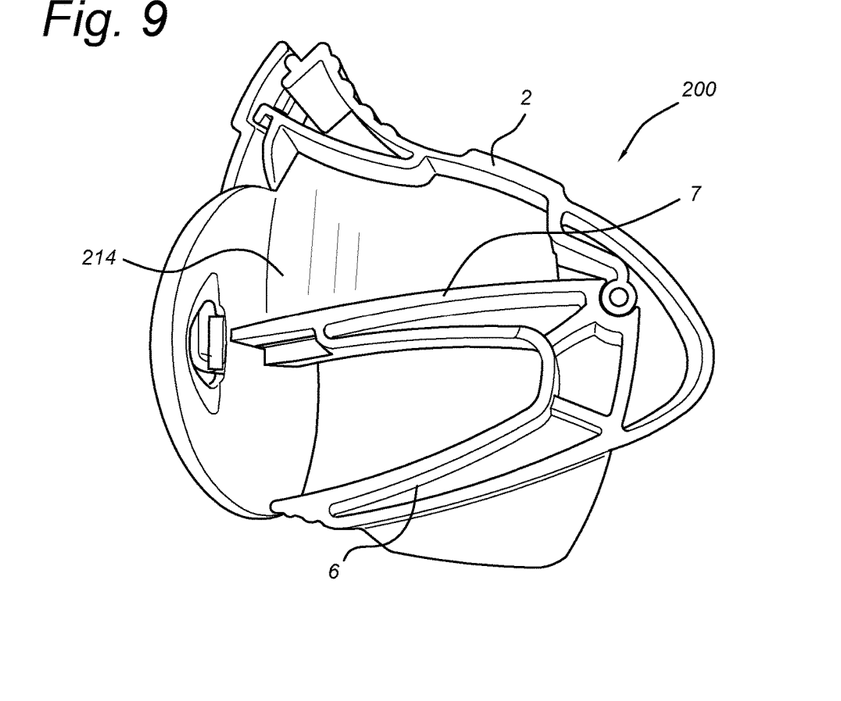
FIG. 9 shows the embodiment of FIG. 7 in the initial position with a safety device connected.

FIGS. 7-9 show a further embodiment of the present invention. Surgical instrument 200 includes similar parts to those of surgical instrument 1 shown in FIGS. 1-5, and operates in a similar manner Similar parts are labelled with similar numbers.

Surgical instrument 200 has first pivoting leg 2, blade 3 and U-shaped member 5 comprising second leg 6 and third leg 7. In the embodiment shown in FIGS. 7-9 first pivoting leg 2 comprises upper biasing member 202 with protrusion 204 and lower biasing member 206 with protrusion 208; and elongated member 13 comprises first detent groove 210 and locking groove 212. Blade 3 connects to lower biasing member 206, and upper biasing member 202 pushes away from lower biasing member 206.

Surgical instrument 200 initial position starts with protrusion 208 engaging first detent groove 210 at the upper end of the safety mechanism, as shown in FIG. 7. First detent groove 210 in the upper part of the elongated member 13 is dimensioned to accommodate protrusion 208 of lower biasing member 206. First detent groove has a first side wall located on the upper part which is perpendicular to its bottom wall to retain protrusion 208. The inclined interior wall of elongated member 13, starting from its upper free end, will facilitate introduction of protrusion 208 into said first detent groove 210 to go from the position of FIG. 7 to the position shown in FIG. 8.

Elongated member 13 will also flex distal.

To move leg 2 further toward the closed position, elongated member 13 can flex and move to the left, and protrusion 208 will leave first detent groove 210. The threshold pressure necessary to overcome the detent and start movement from the initial position, shown in FIG. 7, to the closed position, shown in FIG. 8, will depend on the flexing characteristics of first leg 2, upper and lower biasing members 202, 206, elongated member 13, and profiles of the detent groove 210 and protrusions 208 and 204, which can easily be determined and adapted by the skilled person depending on the needs to avoid any unintentional movement of the blade 3 while in the initial position of FIG. 7.

If the threshold pressure has been exceeded, first leg 2 will move toward the closed position. Protrusion 204 can be shaped so that it is not able to engage first detent groove 210, and will only enter second locking groove 212 in the lower part of elongated member 13. Pressure will move first leg 2 toward closed position with protrusion 208 first entering locking groove 212, followed by protrusion 204 from upper biasing member 202 entering locking groove 212. Upper side wall of locking groove 212 is designed to keep protrusion 204 inside it. Upper biasing member 202 protrusion 204 engages groove 212, thereby flexing to press lower biasing member 206 and blade 3 downward to ensure blade 3 stays in a closed position so that tip 23 engages lower member 6 to guarantee that blade 3 will perforate the tissue when in operation. At this point, first leg 2 in the closed position can only be liberated by deforming the elongated member 13. Surgical instrument 200 can also include ridges, for example on upper and/or lower biasing members 202, 206, to assist in the closing and/or opening of surgical member 200 and/or the flexing of elongated member 13.

FIG. 9 shows surgical instrument 200 with safety device 214. Safety device 214 connects between first leg 2 and third leg 7, and wraps around third leg 7 to lock surgical instrument 200 in a first position. Safety device 214 can be held in place by small ridges on first leg 2, third leg 7, safety mechanism 13 and/or other means on surgical instrument and/or safety device 214. Safety device 214 can be made of a rigid material, for example, plastic.

When connected to surgical instrument 200, safety device 214 locks surgical instrument 200 into initial position (shown in FIG. 7), and any pressure on upper biasing member 202 will not result in any movement of leg 2. This ensures that blade 3 is kept in a safe position when surgical instrument is not in use. When ready for use, safety device 214 can be pulled off surgical device 200, overcoming any ridges and/or snaps holding safety device 214 in place, and surgical instrument 200 first leg 2 can move as described above.

The described surgical instruments can be used for several surgical interventions. Two main applications are episiotomy and caesarean section.

When using surgical instrument 1 for performing an episiotomy the medical practitioner will first bring the first leg to the initial position as shown in FIG. 4, having first leg 2 engaged to the elongated member 13 of the safety mechanism.

Afterwards second leg 6 will be inserted into the vagina until the selected point for initiating the incision in the perineum is reached. At this point the first leg 2 will be pressed by using the thumb such that when the threshold pressure value is exceeded, the blade 3 will pass the slit 20 leaving the initial position. The tip 23 of the blade 3 will thus perforate that point of the perineum coinciding with the trajectory of the blade 3 when moving from the initial position to the closed position. The medical practitioner will now pull the instrument outwards of the vagina and the perineum will be cut towards its free edge due to the effect of the cutting edge 22 of the blade. This method using the described instrument ensures that incision will only be performed when the medical practitioner moves the instrument in the direction of the free edge and no unintentional cut will occur. Since the incision is performed from the inside to the free edge a gradual and assured reduction of tensions prevailing at the free edge is further obtained.

The above described surgical instruments can also be used for performing a caesarean section. For this purpose a method for performing a caesarean using the above described surgical instrument 1 is described. The medical practitioner will first perform a puncture in the patient's abdominal and uterus walls. The medical practitioner, after bringing the surgical instrument to the engaged initial position of FIG. 4, will introduce the second leg 6 into the orifice and the uterus of the patient in a first direction to perform the incision, generally perpendicular to the sagittal plane of the patient. After introduction of the instrument together with at least the first finger, the medical practitioner will bring the first leg to the closed position of FIG. 5 such that a perforation in the abdominal and uterus walls, remote from the orifice, is made. By pulling the instrument in the direction of the orifice the incision of that portion will be performed. If it is necessary to have a larger incision, after bringing again the instrument to the initial engaged position of FIG. 4, the medical practitioner will introduce again the second leg 6 in the orifice and in a second direction, generally opposite to the first direction. By closing the instrument to the closed position of FIG. 5 and pulling in the direction of the orifice the caesarean section will be completed. The embodiment of FIG. 6 is particularly adapted for performing a caesarean section, where limited access may be available, due to the narrow width and single finger operation of the lower leg 106.

As the skilled person would understand, the above described surgical instrument can be used for performing an incision in the wall of any cavity in a human or animal body following a similar method as described above for the caesarean and episiotomy, wherein the instrument has to be inserted through an aperture in said wall.

The invention claimed is:

1. A surgical instrument for performing an incision at a free edge of a portion of tissue, comprising:
    first and second pivoting legs movable towards each other with respect to a fixed end, and defining a receiving space between the legs configured to receive the free edge of the portion of tissue,
    the surgical instrument having an initial position with opened legs and a closed position, where no further closing movement of the pivoting legs towards each other is possible,
    a tissue perforating member located at a free end of the first leg and extending into the receiving space at a distance from the fixed end, such that when the legs are in the closed position, the tissue can be perforated at a perforation location separated from the free edge of the tissue, while an uncut tissue band remains between the perforation location and the free edge,
    an intermediate third leg in between the first and second legs and fixed with respect to the second leg, the receiving space further being defined by a space between the second and third legs and wherein the third leg comprises a slit at its free end for accommodating movement of the perforating member between the initial position and the closed position and a pivot groove for accommodating a protruding member of the first leg to form a hinge such that the first leg can pivot in relation to the third leg, and
    a safety mechanism at the free end of the third leg arranged to selectively retain the first leg in the initial position, such that the perforating member does not enter the receiving space, the safety mechanism being releasable to allow movement of the first leg to the closed position;
    wherein the safety mechanism is configured such that when the surgical instrument is in the initial position it covers the perforating member, closing a space between the free ends of the first and third legs;
    wherein the perforating member comprises a blade with a cutting edge facing the fixed end, such that movement of the surgical instrument in the direction of the free edge will cause incision of the tissue band.

2. The surgical instrument according to claim 1, the safety mechanism comprising a detent groove for engagement by the first leg to keep the instrument in the initial position.

3. The surgical instrument according to claim 1, wherein the safety mechanism is configured to allow further movement between the initial and the closed position when a threshold pressure on the first leg enough to disengage it from the safety mechanism is exceeded.

4. The surgical instrument according to claim 1, wherein the safety mechanism comprises a locking groove to be engaged by the first leg to reversibly lock the surgical instrument in the closed position.

5. The surgical instrument according to claim 1, further comprising a safety device engageable with the surgical instrument to prevent movement from the initial position to the closed position.

* * * * *